United States Patent [19]

Cleary et al.

[11] Patent Number: 5,271,940
[45] Date of Patent: Dec. 21, 1993

[54] TRANSDERMAL DELIVERY DEVICE HAVING DELAYED ONSET

[75] Inventors: Gary W. Cleary, San Mateo; Kenneth J. Colley, San Francisco; Jesus Miranda, Menlo Park, all of Calif.

[73] Assignee: Cygnus Therapeutic Systems, Redwood City, Calif.

[21] Appl. No.: 860,300

[22] Filed: Mar. 27, 1992

Related U.S. Application Data

[63] Continuation of Ser. No. 407,476, Sep. 14, 1989, abandoned.

[51] Int. Cl.⁵ .................................... A61F 13/00
[52] U.S. Cl. .................................... 424/448; 424/443; 424/448
[58] Field of Search ................ 424/448, 449, 443, 447

[56] References Cited

U.S. PATENT DOCUMENTS

| | | | |
|---|---|---|---|
| 3,703,890 | 11/1972 | Saunders, Jr. .................. | 128/2 |
| 4,117,841 | 10/1978 | Perrotta et al. .................. | 424/448 |
| 4,286,592 | 9/1981 | Chandrasekaran ................ | 424/448 |
| 4,812,305 | 3/1989 | Vocal ............................... | 424/448 |
| 4,839,174 | 6/1989 | Baker et al. ...................... | 424/449 |
| 4,858,604 | 8/1989 | Konishi ........................... | 604/306 |
| 4,877,618 | 10/1989 | Reed, Jr. ......................... | 424/448 |
| 4,956,181 | 9/1990 | Bayh et al. ...................... | 424/448 |

FOREIGN PATENT DOCUMENTS 0249343 12/1987 European Pat. Off. .
0290262 11/1988 European Pat. Off. .

OTHER PUBLICATIONS

EPA Publication No. 0290262 A2.

*Primary Examiner*—Paul R. Michl
*Assistant Examiner*—Leon R. Horne
*Attorney, Agent, or Firm*—Morrison & Foerster

[57] ABSTRACT

A transdermal delivery device has a reservoir containing an active compound, which is kept separate from the delivery layers of the device until administration. At the time of administration, the reservoir is laminated to the delivery layers, or is ruptured to place the active compound, vehicle, and/or permeation enhancers in contact with the delivery layers, which results in administration of the active compound to the skin after a delay period.

23 Claims, 5 Drawing Sheets

TRANSDERMAL DELIVERY DEVICE HAVING DELAYED ONSET

This application is a continuation of application Ser. No. 07/407,476, filed Sep. 14, 1989, abandoned.

TECHNICAL FIELD

This invention relates to devices and methods for administering biologically active compounds through the skin, i.e., transdermally. More specifically, the invention relates to a device and method for transdermal delivery having a delayed onset of delivery.

BACKGROUND OF THE INVENTION

The delivery of compounds through the skin provides many advantages. Primarily, transdermal delivery provides a comfortable, convenient, and noninvasive means for delivering drugs. By avoiding administration through the gastrointestinal tract, one may employ compounds which would otherwise be degraded, metabolically deactivated, or poorly absorbed. Additionally, one eliminates the complications of gastrointestinal irritation. Transdermal delivery using a continuous-release type of device also allows one to terminate administration immediately should the need arise, e.g., in the event of an adverse drug reaction, or over-elevation of drug plasma concentration.

Drug delivery devices may generally be classified as either "matrix" or "reservoir" in construction. A matrix or monolithic device generally comprises a drug-permeable solid polymer, having a drug dispersed throughout. Matrix devices may be formed from erodible or non-erodible polymers (transdermal devices are typically non-erodible). Reservoir devices generally comprise a depot of essentially pure drug (or drug with excipient) surrounded by a rate-controlling membrane, where the rate of drug diffusion through the membrane controls the rate of release. Combinations of matrix reservoirs with rate-controlling membranes have also been proposed. The typical design criteria are to provide a substantially constant and continuous release rate, and to provide a release rate capable of delivering a therapeutically effective amount of the compound. Additionally, the device must be non-irritating, and is preferably designed to be of a convenient size.

The conventional transdermal device is designed with the goal of delivering a therapeutic compound at a substantially constant rate ("zero-order" delivery). However, administration of some compounds at a constant, continuous rate may cause drug tolerance to develop. In order to prevent tolerance, a transdermal patch-type device must be removed periodically to interrupt continuous delivery. This in turn creates additional problems of patient compliance and design of the patch adhesive (which must adhere to the skin continuously), and fails to accommodate the patient's circadian rhythms.

Nitroglycerin is a vasodilator currently administered for coronary disorders, especially angina pectoris and congestive heart failure. As nitroglycerin cannot be administered orally, it is typically administered sublingually, or via transdermal patch. Commercially available patches, such as Transderm Nitro ® and Nitro-Dur ®, provide essentially constant plasma concentrations of nitroglycerin over a 24 hour period, and are changed daily. However, recent studies suggest that continuous administration of nitroglycerin induces tolerance, with concomitant loss of efficacy in the patient.

There are a large number of patents disclosing drug delivery devices. General transdermal devices are disclosed in Zaffaroni, U.S. Pat. No. 3,742,951; 3,797,494; 3,854,480; 3,921,636; 3,996,934; Baker, U.S. Pat. No. 3,923,989; Gerstel et al, U.S. Pat. No. 3,964,482; Shaw et al, U.S. Pat. No. 4,650,484; 4,704,119; Gale, U.S. Pat. No. 4,661,105; 4,698,062; Eckenhoff et al, U.S. Pat. No. 4,717,568; and Magruder et al, U.S. Pat. No. 4,723,957. Devices for transdermal administration of nitroglycerin are disclosed by Blank, U.S. Pat. No. 4,533,540; Enscore et al, U.S. Pat. No. 4,559,222; Gale et al, U.S. Pat. No. 4,615,699; 4,681,454; 4,681,584; Leslie et al, U.S. Pat. No. 4,654,209; Theeuwes et al, U.S. Pat. No. 4,655,766; Andirola et al, U.S. Pat. No. 4,661,441; Wick, U.S. Pat. No. 4,751,087; Guse et al, U.S. Pat. No. 4,776,850; 4,778,678; Berry et al, U.S. Pat. No. 4,784,857; and Wagle et al, U.S. Pat. No. 4,786,282. However, these references do not teach transdermal delivery devices having a delayed onset of administration.

DISCLOSURE OF THE INVENTION

The device of the invention provides a continuous, constant transdermal release of an active substance, wherein the onset of release is delayed from 1-24 hours, depending on the length of time that the drug is delivered. This provides a "wash out" period, during which the plasma concentration of any compound remaining in the patient's system from application of the previous device is allowed to drop to near baseline levels. Accordingly, a patient may wear the patch for 24 hours, replacing the patch with a fresh patch prior to going to sleep. The wash out period thus occurs during the patient's sleep, and is followed by effective plasma concentrations of the active compound during the waking hours.

One aspect of the invention is a device for the transdermal administration of active compounds to a subject, wherein release of the compound is delayed for 1-24 hours after the device is applied to the subject's skin. Another aspect of the invention is a kit, which may be assembled by the patient to provide a transdermal device exhibiting delayed release. In another embodiment, the device is supplied in a fully-assembled form, having the active compound sequestered within a capsule prior to activation by the user. This activation allows the drug, vehicle, and/or enhancer to begin permeating the patch just prior to application. The capsule (in its intact form) may be completely impermeable to the capsule contents, thus allowing the use of highly volatile active compounds, vehicles, and enhancers. In a presently preferred embodiment, the device further includes a delay layer, which futher retards diffusion of the active compounds, vehicles, and/or enhancers toward the skin contact surface of the patch.

Another aspect of the invention is a method for treating a subject with an active compound susceptible to development of tolerance, by applying the device of the invention having a delayed onset of release sufficient to allow elimination of the compound from the subject's body from the previous patch, to levels low enough to avoid induction of tolerance.

MODES OF CARRYING OUT THE INVENTION

A. Definitions

The term "active compound" as used herein refers to any substance which may be administered to an animal to obtain a beneficial effect. Active compounds may be drugs, for example, vasodilators such as nitroglycerin, amyl nitrate, isosorbide dinitrate or mononitrate and the like, L-DOPA, analgesics, antiinflammatories, antihistamines, antibiotics, antihypertensives, hormones, and the like, which are useful for preventing or ameliorating a given disorder. Other active compounds include contraceptives (e.g., estradiol, levonorgestrel, 3-ketodesogestrel, gestodene, and the like), vitamins, appetite suppressants, nicotine, caffeine and other stimulants, growth promoters (particularly when administered to livestock), and the like. Suitable active compounds within the scope of this invention are capable of diffusion or absorption through the skin.

The term "mammals" includes animals such as humans, livestock including cattle, sheep, goats, horses, small animals such as dogs, cats, and mice, wildlife and zoo animals such as elephants, lions, tigers, antelope, and the like. The term "animal" refers to mammals and birds, including domestic fowl such as chickens, geese, ducks, turkeys, game hens, and the like.

The term "liquid carrier" refers to a solvent compatible with the reservoir matrix and adhesive layers, as well as with skin, in which the active compound is soluble. The active compound will preferably be moderately soluble in the carrier. Suitable carriers generally enhance the release rate of active compound from devices of the invention. Exemplary carriers include lower alcohols such as methanol, ethanol, propanol, isopropanol, and the like, glycols such as propylene glycol and the like, glycol ethers and esters, dimethylsulfoxide, tetrahydrofuran, acetone, and the like.

The term "delayed onset" as used herein refers to the situation where no active compound is released from the device of the invention until some time after the device is applied to the skin. For a 24 hour patch, this delay period will typically be 1-18 hours, preferably about 12 hours in duration. Patches designed for longer duration (e.g., a weekly patch) may have correspondingly longer delay periods.

B. General Method

Figure 1:
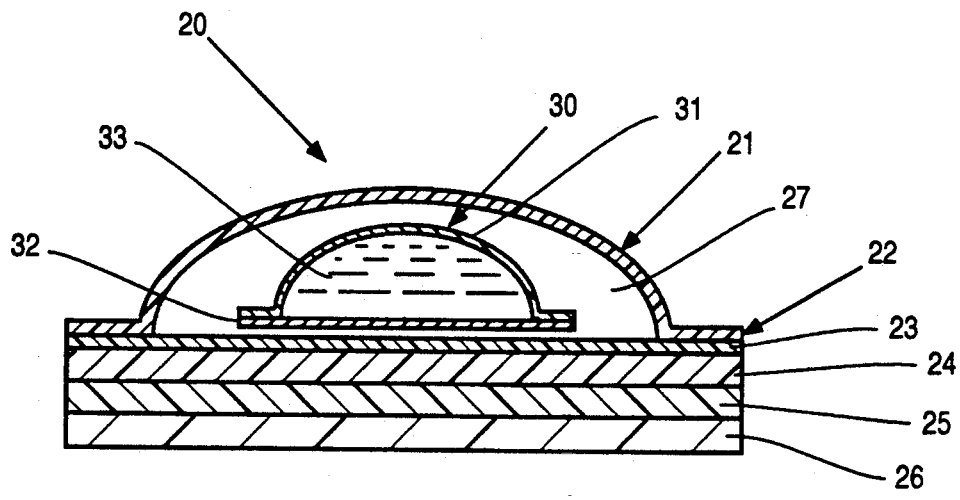
FIG. 1 shows a schematic cross-section of a presently preferred embodiment of the invention, wherein the active compound is sequestered within a rupturable capsule.

FIG. 1 depicts a presently preferred device of the invention, having a rupturable capsule containing the active compound prior to administration. This embodiment 20 comprises an optional wick layer 23, which is capable of diffusing the active compound, but which does not act as a reservoir: the wick layer preferably does not absorb the active compound to a significant degree, and thus does not retain a substantial amount of the compound. The wick layer is preferably formed from a non-woven fabric, and must be capable of adhering to the adjacent layers under conditions of use (e.g., when saturated with active compound and vehicle). A non-permeable backing layer 21 forms the outer surface of the device, and prevents loss of the active compound through the upper surface. The backing layer is preferably occlusive, waterproof, drug-proof (for at least the administration period of the device), and suitable for lamination to the adjacent layer (wick layer 23 if present, support or delay layer 24 if present in the absence of wick layer, or skin contact adhesive layer 25 if neither the wick layer nor the support/delay layer are present). Backing layer 21 may be heat-sealed or crimped onto the adjacent layer, forming a perimeter region 22, which seals the reservoir area 27 formed by the void between backing layer 21 and the adjacent layer (23, 24, or 25).

Backing layer 21 and the layer adjacent (23, 24, or 25) are laminated together to form a reservoir volume 27. The reservoir volume is a space that contains rupturable capsule 30, comprising the active compound 33, optionally a vehicle, permeation enhancer, solubilizer, and the like, sealed within a non-permeable film wall material 31. The reservoir volume 27 may also contain a carrier or vehicle, or may be empty. Capsule 30 is maintained in an intact state, so that no active compound 33 is within the reservoir volume, exposed to the wick layer (or other adjacent layer) prior to administration. The capsule may be fabricated from any material which is impermeable to the active compound and its vehicle, and which may be ruptured when desired to release the active compound (and carrier if present) and activate the device. The ability to use a completely impermeable capsule allows one to employ compounds which are normally precluded from use in transdermal devices due to their volatility. Because the volatile compound will be completely contained within the internal capsule, one may employ vehicles and enhancers such as ethanol, acetone, methanol, ethyl acetate and the like, or use active compounds such as nicotine, without loss of compound from the device prior to administration. Devices of the prior art must be permeable to the compounds contained therein, and thus tend to lose any volatile components during shipping and storage prior to administration. (Even if the volatile components are contained with the prior art device within a pouch, the components will not be distributed properly within the device at the time of administration.) Rupturable capsules may have a rupturable seal at a seam (or other deliberately weakened portion of the wall), or may be prepared from a fragile or frangible material (for example, glass, silica, crystalline or brittle polymers, etc.), either crushable or having a scored portion to allow rupture by flexing the patch. Thus, in a presently preferred embodiment, the capsule is formed from an aluminum foil-laminated heat seal film having a rupturable heat seal 32. This film is flexible, and comprises a layer of aluminum (about 0.3-1 mil) with a heat seal layer comprising EVA, polypropylene, or modified polyethylene (about 0.3-0.8 mil). However, the capsule may be fashioned from any frangible or friable container or film. For example, a thin glass capsule or brittle (e.g., crystalline) polymer may alternatively be employed. If desired, the capsule may be scored or necked to enhance breaking. The capsule may be attached to the backing layer 21 or the layer adjacent the backing layer (23, 24, or 25), or may be simply encapsulated within the reservoir volume 27 in loose form.

The delay layer may consist of the wick layer 23, a specific delay layer or structural layer 24, or contact adhesive layer 25, or any combination thereof. The delay layer may be an adhesive layer or a permeable film. This layer contributes structural integrity to the device, as well as a means to delay the permeation of the drug through the device to the skin. It is presently preferred to include either a film layer or an adhesive layer (in combination with a wick layer), as this structure helps prevent the device from curling. The layer must be capable of lamination to the adjacent layers (contact adhesive layer 25, and wick layer 23 if present, backing layer 21 if the wick layer is not present). In embodiments wherein the wick layer 23 is absent, it is preferred to employ a structural layer 24 in the form of a film. Suitable films for the delay layer include, without limitation, dense or microporous films of about 0.5-3.0 mil in thickness composed of, for example, polypropylene (e.g., Celgard, available from Celanese), polyethylene (available from, e.g., 3M), or polytetrafluoroethylene (for example Teflon, available from Gore-tex). Suitable adhesives, which may be employed as a delay layer, include polysiloxanes, polyisobutylenes, polyacrylates, polyurethanes, ethylenevinyl acetate copolymers, low molecular weight polyether amide block polymers (e.g., PEBAX), polyisobutene, polystyrene-isoprene copolymers, polystyrene-butadiene copolymers, and mixtures thereof. The presently preferred delay membranes are microporous polypropylene (Celgard), microporous polyethylene (3M), microporous polytetrafluoroethylene (e.g., Teflon, Gore-tex), and dense membrane polyurethanes, polyacrylates, and polyisobutylenes. "Dense membranes" are those membranes which retard permeation of the active compound to a significant degree.

Skin contact adhesive layer 25 is a pressuresensitive adhesive suitable for application to human skin. The adhesive selected must also be compatible with the active compound and its vehicle, and must be suitable for lamination to the upper layers. Presently preferred contact layer adhesives include acrylic, silicone, polyisobutylene, polyurethane, SIS, and SBS pressure sensitive adhesives. The layer may range in thickness from about 0.5 to about 5.0 mil. The adhesive layer is preferably protected prior to administration by means of a release liner 26, which is generally a thin film or sheet which has been treated to allow easy removal from the adhesive layer. In this device, the active compound is sequestered within a non-permeable capsule prior to activation: accordingly, the release liner need only protect the contact adhesive, without regard for the nature of the active compound since the release liner is not exposed to the active compound during storage. In other words, the release liner need not be impermeable to the active compound, thus making available a wider range of materials. Thus, siliconized or fluorocarbon-treated paper or polystyrene may be used, in place of more expensive polymer films such as polyester or polycarbonate, which might otherwise be required. The thickness of the release liner is not critical, and may be determined by aesthetic criteria. In general, the release liner must exhibit sufficient thickness and structural integrity that it may be peeled or stripped easily from the contact adhesive layer, preferably in one or two pieces. A thickness of about 3 mil is generally sufficient.

As this embodiment sequesters the active compound completely prior to activation, it is much simpler to package. I.e., the package need not be impermeable to the active compound, as the compound will be completely contained within the device. Thus, one may employ simple cardboard or plastic containers, paper or plastic pouches, and the like. If desired, the release liner may be provided in the form of a long strip with multiple perforations spaced at appropriate intervals, such that the device of the invention may be provided on "tear-off" rolls or accordion-pleated stacks. Thus, a sufficient number of devices to treat a patient for a month can be provided on one strip, or within one container. Additionally, each device can then be numbered or dated, to aid patients in compliance. For example, on the fourth day of the month, the patient can determine if he or she has already applied the device for the day by determining whether or not the device marked "4" has been removed yet. This is a significant advantage for devices which are applied on a daily or weekly basis over an extended period of time.

Figure 5:
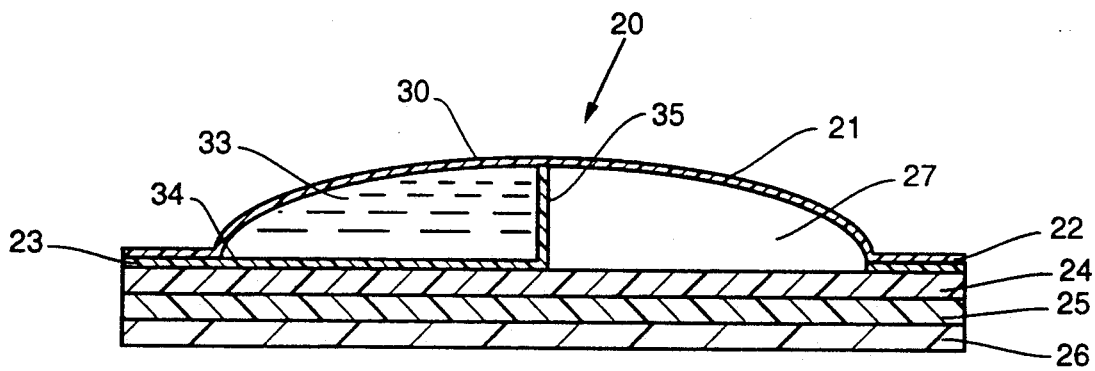
FIG. 5 is a schematic cross section of another presently preferred embodiment, having a rupturable capsule formed as part of the drug reservoir of the device.

Another embodiment of the invention is shown in FIG. 5. In this variation, the rupturable capsule is provided as part of the backing layer 21, rather than as a separate layer 31. In this case, an impermeable layer 34 is laminated to the wick layer 23, and a rupturable membrane or film 35 is provided to separate the reservoir volume 27 in contact with the wick layer from the sequestered portion.

Figure 6:
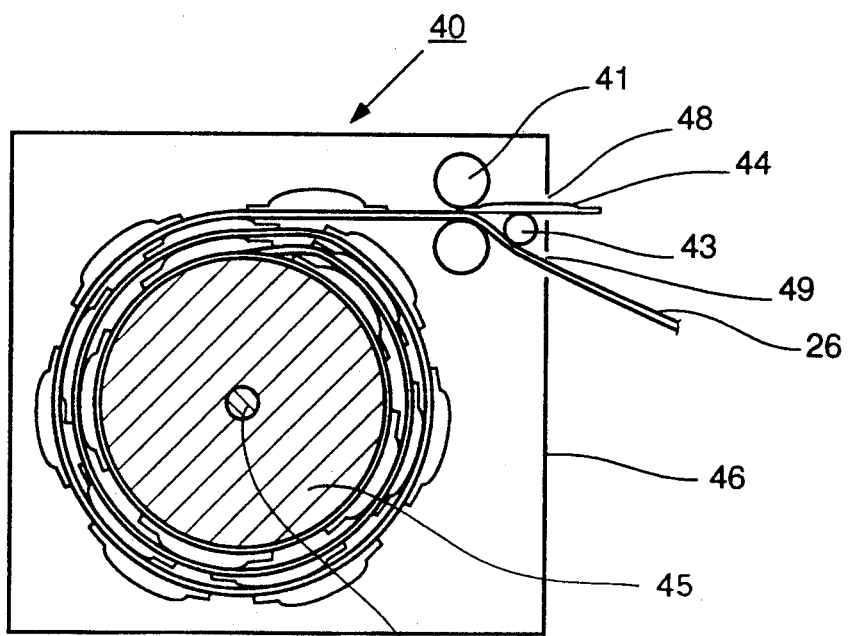
FIG. 6 is a cross section of a dispensing device, suitable for dispensing devices of the invention as shown in FIG. 1 or FIG. 5.

Finally, the device may be packaged in a container which provides for capsule rupture and/or release liner removal automatically upon removal. Such a device is depicted in FIG. 6. The container may be a box 46 of any suitable shape, having pressure means 41 and 42 above and below an aperture 48 sized to admit the device 44 after capsule rupture. A plurality of devices are provided on a long carrier strip 26, wound in a roll around a wide-diameter spool 45 (wide enough to avoid premature capsule rupture due to flexing). To dispense the device, the carrier passes through pressure means 41 and 42, rupturing the capsule, and then passes through aperture 48. The pressure means may be a pair of pressure rollers as depicted, a roller opposed to a flat surface, or simply two flat surfaces having a separation decreasing in the direction of travel as the device is dispensed. The pressure means is preferably a cam-shaped roller. The pressure means may optionally be tensioned by means of a spring or other device (not shown). The device may further comprise means for separating the carrier/liner 26 from the device, such as roller 43. In this embodiment, carrier 26 may be ejected through a separate aperture 49. The spool 45 may optionally comprise an axle 47 affixed to the interior of the enclosure 46. If desired, the axle 47 may be further connected to a handle or crank (not shown), by which the carrier roll may be advanced and the devices of the invention dispensed. Alternatively, the devices may be dispensed by simply pulling the carrier strip 26 until the device is ejected. In this embodiment, the carrier selected must be strong enough to pull the device through the pressure means. The pressure means must be far enough from the carrier separation means 43 (if present) that the device has completely passed the pressure means and the capsule ruptured prior to separation from the carrier. Other devices not pictured may easily be constructed. For example, the roll of patches may be replaced with an accordion-folded stack of patches on a pleated carrier. The pressure means may be crank operated rather than the supply roll (particularly when the pressure means are rollers). In the event a frangible, scored capsule is used, the device may be designed to bend the capsule until ruptured. Other variations will be apparent to those of ordinary skill in the art.

Referring to FIGS. 1 and 5, capsule 31 is ruptured by applying pressure so that the active compound is released from the capsule into the reservoir volume 27. This may be accomplished by placing the device on a flat surface and pressing the capsule with a finger or thumb, or by some external pressure such as passing the device through a suitable mechanical pressure device, such as a pair of rollers (similar to a mangle as found on old cloths washing machines), or by bending or flexing the patch to cause rupture of a weakened or scored area. The release liner 26 is removed from contact layer 25, and the device applied to a suitable area of intact skin, for example the upper arm, thigh, chest, lower abdomen, and the like. Alternatively, the device may be applied to the skin prior to activation by rupturing the capsule. Upon rupture, the active compound and vehicle are released from the capsule, and diffuse through the adjacent layers. Where a wick layer is present, the wick layer acts to spread the active compound over the entire available layer, providing for an even flow across the area of the device. The compound diffuses through the wick layer (if present), the structural layer (if present), and into the contact layer, where it accumulates until sufficient concentration has developed that diffusion into the patient's skin begins at a significant rate. Due to the fact that the intermediate layers are not equilibrated with the compound, a substantial delay occurs prior to significant diffusion into the skin. This delay is preferably about 8–12 hours, and may be adjusted by selection of appropriate layer and vehicle materials.

Figure 2:
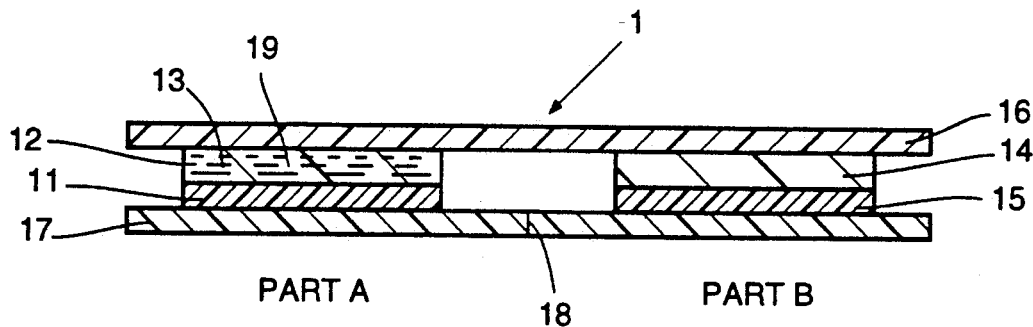
FIG. 2 is a schematic cross-section of a kit embodiment of the invention which is laminated by the user. The layers depicted are thin solid films, preferably flexible and/or elastomeric, and are laminated together immediately prior to application by the user. The view depicted illustrates a cross-section of the device with the protective release liner and liner/carrier in place.

FIG. 2 shows another embodiment of the invention 1, having a polymeric matrix reservoir layer 12 containing an active compound 13 and optionally a liquid carrier 19. This reservoir layer is laminated permanently to an impermeable backing layer 11, which prevents loss of active compound from the "non-contact" side of the device, and which may additionally provide some degree of structural support. Although layers 11 and 12 are shown here as distinct layers, the backing layer may be formed from a portion of the matrix reservoir layer by suitable treatment, such as heat, chemical crosslinking, radiation, and the like, so as to render the surface substantially impermeable to the active compound and carrier (if present). Layer 11 is preferably supported by a liner/carrier 17. The reservoir layer 12 is preferably protected on its other side (opposite backing 11) by a releasable protective liner 16. A contact adhesive layer 14 is provided which is not in contact with said reservoir layer 12, and may serve as the delay layer. Adhesive layer 14 is substantially free of active compound 13, although it may contain a liquid carrier, permeation enhancer or the like if desired. An additional release liner 15 may be laminated to adhesive layer 14 if desired. The release liner 15 and adhesive layer 14 are supported by a liner/carrier, preferably the same liner/carrier 17 which supports reservoir 12 and backing 11. The adhesive layer 14 is preferably protected on its upper surface (opposite optional release liner 15) by an additional releasable protective liner, preferably an extension of said protective liner 16. An additional delay layer (not shown) may be laminated between contact adhesive layer 14 and protective liner 16, if desired.

Figure 3:
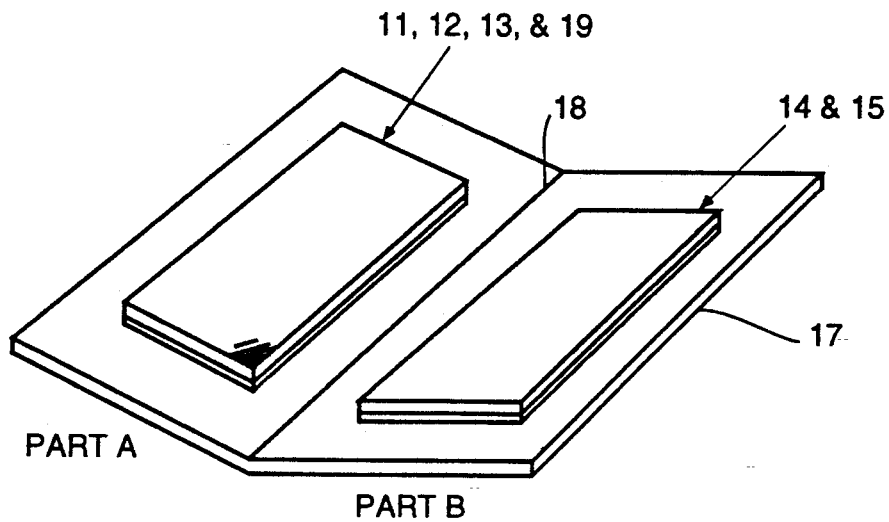
FIG. 3 shows a perspective view of the kit embodiment after removal of the upper release liner, just prior to lamination.
Figure 4:
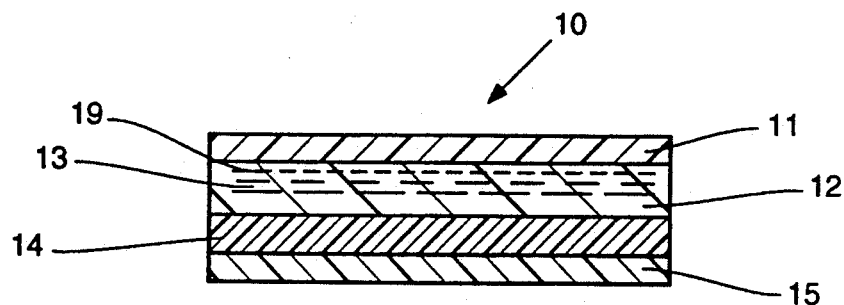
FIG. 4 depicts a schematic cross section of the kit embodiment immediately after lamination, following removal of the liner/carrier.

To use the device of FIG. 2, the protective liner 16 is first removed from the upper surface of the device. The exposed surface of adhesive layer 14 is then laminated to the exposed surface of reservoir layer 12. In devices wherein both layer 12 and layer 14 are supported by the same carrier 17, this lamination is preferably assisted by means of a crease or fold line 18, as shown in FIG. 3. Lamination is accomplished by simply folding the device along the fold line, and pressing layer 14 onto layer 12. It is preferred that the reservoir-backing sublaminate and the adhesive-liner sublaminate be arranged on the liner/carrier so that folding the liner/carrier along the crease insures that the completed device layers will overlap completely. This results in the configuration shown in FIG. 4. At this point, liner/carrier 17 is removed from layer 14 (or release liner 15 if present). If release liner 15 is present, it also is removed, and the exposed adhesive layer 14 applied to the subject's skin. Carrier 17 is then removed from backing layer 11, leaving the device comprising layers 11, 12, and 14 on the subject's skin. Active compound 13 (and optionally liquid carrier 19) then begins to diffuse into layer 14, and finally into the subject's epidermis. A substantial time delay occurs before the active compound begins to diffuse into the epidermis at a significant rate, due to the fact that layer 14 is not equilibrated with reservoir 12 at the time of application.

The device of the invention is particularly suited for repeated administration. When used to administer nitroglycerine (e.g., for treatment of congestive heart failure) or nicotine (e.g., to reduce cigarette craving), a device of the invention is preferably applied shortly before retiring for the evening. Due to the delayed onset of release, little or no compound is released while the subject is sleeping. Instead, compound is released at or just before time for the subject to wake up, when the compound is most needed. The device continues to release active compound over the next sixteen hours. Then, the device is removed, and is replaced with a fresh device. Thus, the plasma level of active compound may decline to baseline during the subject's sleep, so that tolerance or undesirable side effects do not develop. In the case of appetite suppressants, it is preferred to apply a device of the invention shortly before breakfast. Thus, the subject is able to eat a healthy breakfast, with appetite suppression occurring several hours later, when most needed.

Backing layer 11 and 21 is preferably made of a sheet or film of a preferably flexible elastomeric material that is substantially impermeable to the active compound. The layer is preferably on the order of 0.0005 to 0.003" in thickness, and may optionally be pigmented (e.g., to resemble the subject's skin color). Ideally, the layer is fabricated from a material that permits the device to mimic the contours of the skin and to be worn comfortably on areas of skin such as joints or other points of flexure normally subjected to mechanical strain. This reduces the possibility of disengaging or losing the device due to differences in flexibility or resiliency of the skin and the device. Exemplary elastomeric polymers useful for preparing backing layer 11 include polyether block amide copolymers (e.g., PEBAX copolymers), polyethylene methylmethacrylate block copolymers (EMA) such as NUKRELL polymers, polyurethanes such as PELLATHANE or ESTANE polymers, silicone elastomers, polyester block copolymers such as HYTREL, rubber-based polyisobutylene, styrene, and styrene-butadiene and styrene-isoprene copolymers. Flexible polymers include polyethylene, polypropylene, and polyesters such as polyester terephthalate (PET), which may be provided as films or laminates. One may also use laminates or combinations of any of the above materials.

The polymeric matrix reservoir 12 is composed of a polymeric material in which the active compound is poorly to moderately soluble, and capable of diffusing the active compound at a high rate. The reservoir layer must also be capable of adhering to the adjacent layers, to prevent delamination. Thus, selection of the particular material will depend in part upon the active compound (and its vehicle, e.g., solubilizers, permeation enhancers, etc.) selected, and the adhesives employed. Devices of the invention employing a rupturable capsule preferably contain the active compound in the form of a liquid or gel. The vehicle must be capable of flowing following rupture of the sequestering capsule. Typically, the vehicle will comprise silicone fluid, PGML, propylene glycol, other carriers such as lactose, and the like.

The contact adhesive layer 14 and 25 is generally fabricated from an active compound-permeable polymer which adheres to both the reservoir matrix and to mammalian skin without irritation. Exemplary materials for forming layer 14 and 25 include without limitation polysiloxanes, polyisobutylenes, polyacrylates, polyurethanes, plasticized ethylene-vinyl acetate copolymers, low molecular weight polyether block amide copolymers (PEBAX copolymers), and mixtures thereof. The particular material used will depend upon the diffusion coefficient of the active compound (and optionally the liquid carrier) in the adhesive layer, and the diffusion coefficient in the reservoir layer. Generally, both diffusion coefficients should be in the range of about $10^{-5}$ to about $10^{-10}$ cm$^2$/sec.

The various carriers and release liners may be formed from any material having the desired degree of flexibility and impermeability. These liners are generally rendered "strippable" from the contact adhesive layer using silicone or fluorocarbon surface treatments.

The devices of the invention are generally prepared by standard thin-film lamination techniques.

C. Examples

The examples presented below are provided as a further guide to the practitioner of ordinary skill in the art, and are not to be construed as limiting the invention in any way.

EXAMPLE 1

In Vitro Delayed Flux Determination

Water based acrylic adhesive (Flexcryl 1625, 69% solids) was coated onto a 0.003" thick siliconized polyester film at a thickness of 0.010". The adhesive coating was cured at 75° C. for 30 min in order to remove all of the water; cured thickness was 0.004" (10 mg/cm$^2$). A disc of the cured adhesive was die-cut and laminated to the stratum corneum side of a disc of human cadaver epidermis. The skin/adhesive composite was mounted on a glass diffusion cell (effective flux area 0.713 cm$^2$) with the skin side facing the receptor compartment. A measured volume of receiver solution (0.9% NaCl and 0.01% NaN$_3$ in deionized water) was placed in the receptor compartment. The donor was 1.5 g of a nitroglycerin suspension consisting of 2.5 wt % nitroglycerine; 48.8 wt % Dow 360 silicone fluid, 350 cts; 23.8 wt % propylene glycol monolaurate (Gattefasse); and 24.7 wt % lactose. The nitroglycerin suspension was placed in the donor compartment directly in contact with the adhesive. The donor compartment was then occluded, and the cell maintained at 32° C. Samples of the receiving solution were taken periodically and analyzed by HPLC to determine the amount of nitroglycerin permeated per unit time. The experiment was repeated exactly, substituting Nitro-Dur ®, a commercially-available nitroglycerin transdermal device, for the adhesive layer and nitroglycerin vehicle.

Figure 7:
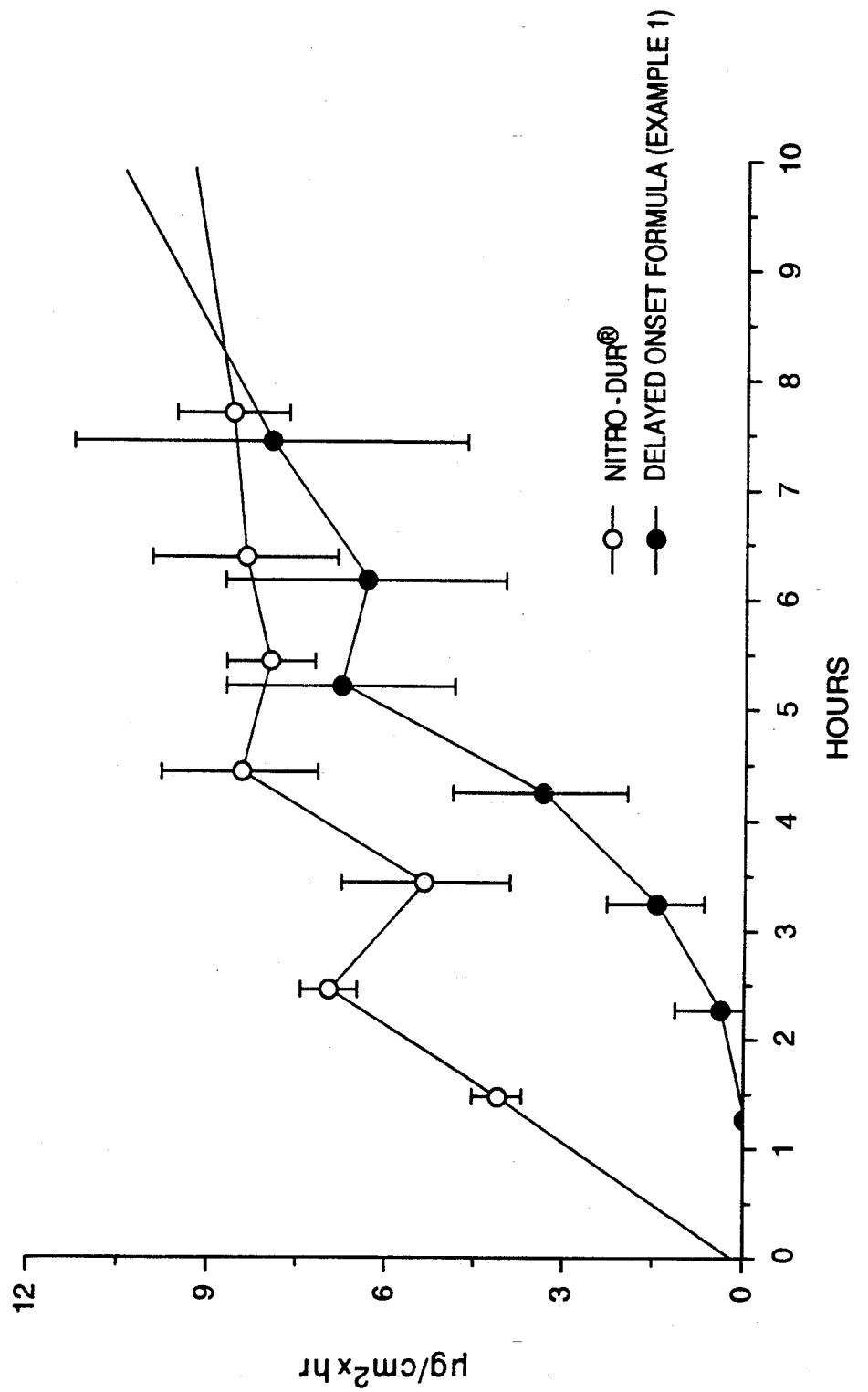
FIG. 7 depicts graphically the results of the experiment reported in Example 1.

FIG. 7 shows the results of this test. Solid circles indicate the amount per cm$^2$ per hour (in micrograms) for the above-described composite. Open circles indicate the results obtained using Nitro-Dur ®. As shown in the Figure, Nitro-Dur ® reached essentially peak flux rate by 2–4 hours after administration, whereas the composition of the invention delayed full onset to 4.5–5 hours after administration.

EXAMPLE 2

In Vitro Delayed Flux Determination

Water based acrylic adhesive (Flexcryl 1625, 69% solids) was coated onto a 0.003" thick siliconized polyester film at a thickness of 0.005". The adhesive coating was cured at 75° C. for 30 min in order to remove all of the water; cured thickness was 0.002" (5 mg/cm$^2$). A disc of the cured adhesive was die-cut and laminated to the stratum corneum side of a disc of human cadaver epidermis. The skin/adhesive composite was mounted on a glass diffusion cell (effective flux area 0.713 cm$^2$) with the skin side facing the receptor compartment. A measured volume of receiver solution (0.9% NaCl and 0.01% NaN$_3$ in deionized water) was placed in the receptor compartment. The donor was 1.5 g of a nitroglycerin suspension consisting of 2.3 wt % nitroglycerine; 75.0 wt % Dow 360 silicone fluid, 350 cts; and 22.5 wt % lactose. The nitroglycerin suspension was placed in the donor compartment directly in contact with the adhesive. The donor compartment was then occluded, and the cell maintained at 32° C. Samples of the receiving solution were taken periodically and analyzed by HPLC to determine the amount of nitroglycerin permeated per unit time. The experiment was repeated exactly, substituting Nitro-Dur ® for the adhesive layer and nitroglycerin vehicle.

Figure 8:
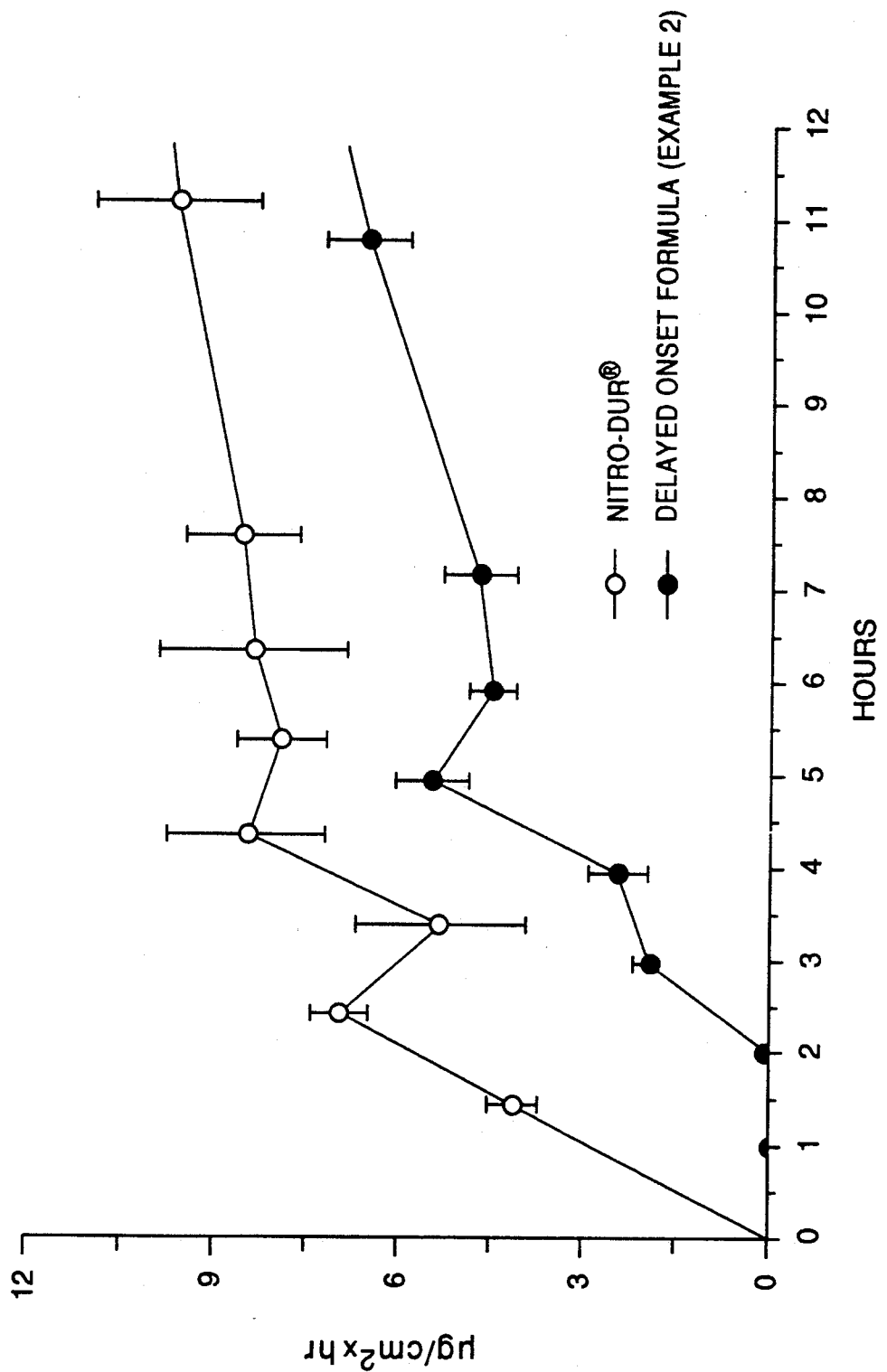
FIG. 8 depicts graphically the results of the experiment reported in Example 2.

FIG. 8 shows the results of this test. Solid circles indicate the amount per cm$^2$ per hour (in micrograms) for the above-described composite. Open circles indicate the results obtained using Nitro-Dur ®. As shown in the Figure, Nitro-Dur ® reached essentially peak flux rate by 2–4 hours after administration, whereas the composition of the invention delayed full onset to 5–6 hours after administration.

EXAMPLE 3

In Vitro Delayed Flux Determination (A) Water based acrylic adhesive (Flexcryl 1625, 69% solids) was coated onto a 0.003" thick siliconized polyester film at a thickness of 0.005". The adhesive coating was cured at 75° C. for 30 min in order to remove all of the water; cured thickness was 0.002" (5 mg/cm$^2$). A disc of the cured adhesive was die-cut and laminated to the stratum corneum side of a disc of human cadaver epidermis. Next, a disc of 2 mil microporous polypropylene membrane (Celgard 2400, available from Celanese/Hoecht) was laminated to the contact adhesive as a delay membrane. The skin/adhesive composite was mounted on a glass diffusion cell (effective flux area 0.713 cm$^2$) with the skin side facing the receptor compartment. A measured volume of receiver solution (0.9% NaCl and 0.01% NaN$_3$ in deionized water) was placed in the receptor compartment. The donor was 1.5 g of a 10 wt % nitroglycerin solution in propylene glycol. The nitroglycerin solution was placed in the donor compartment directly in contact with the adhesive. The donor compartment was then occluded, and the cell maintained at 32° C. Samples of the receiving solution were taken periodically and analyzed by HPLC to determine the amount of nitroglycerin permeated per unit time. The experiment was repeated exactly, substituting Nitro-Dur ® for the adhesive layer and nitroglycerin vehicle.

(B) The procedure described in part A above was repeated exactly, substituting a microporous polypropylene membrane/non-woven polypropylene laminated film (Celgard 4410) for the Celgard 2400 membrane.

Figure 9:
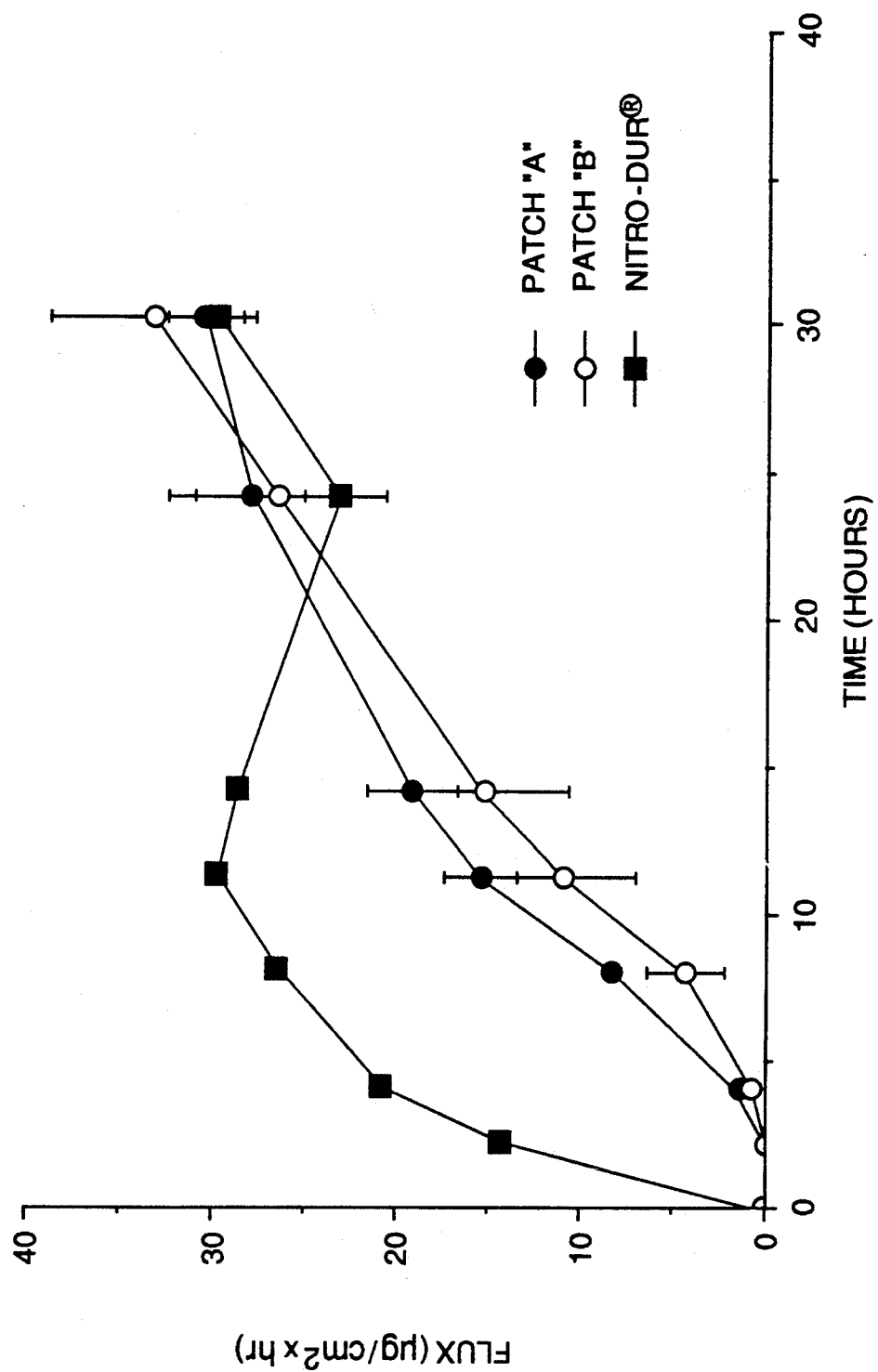
FIG. 9 depicts graphically the results of the experiments reported in Example 3.

(C) FIG. 9 shows the results of these tests. The solid circles depict the results using patch "A" (with Celgard 2400). The open circles depict the results from patch "B" (using Celgard 4410). The solid squares indicate the results obtained using Nitro-Dur ®. As shown in the Figure, Nitro-Dur ® reached a high flux rate by 2-4 hours after administration, whereas the composition of the invention delayed significant onset to 8-12 hours after administration.

What is claimed is:

1. A device for administering an active compound transdermally to a subject's skin, having a delayed onset of delivery, said device consisting essentially of:
    a first layer comprising a polymeric matrix impregnated with said active compound, said compound and matrix being selected to obtain a first compound diffusion coefficient of about $10^{-5}$ to about $10^{-10}$ cm$^2$/sec in said matrix;
    a second layer laminated to said first layer and underlying said first layer, comprising an adhesive capable of adhering to said first layer and to said subject's skin, said second layer being permeable to the active compound in the absence of an activator, said compound having a second diffusion coefficient of about $10^{-5}$ to about $10^{-10}$ cm$^2$/sec in said second layer;
    wherein said second layer is substantially devoid of said active compound at the time said device is applied to said subject's skin and the administration of active compound to the skin is delayed for the time it takes the active compound to diffuse from the first layer through the second layer to the skin.

2. The device of claim 1, which further consists essentially of:
    a backing layer laminated to said first layer opposite said second layer, wherein said backing layer is substantially impermeable to said compound.

3. The device of claim 2, wherein said active compound is selected from the group consisting of nitroglycerin and nicotine.

4. The device of claim 2 wherein said first layer further consists essentially of a liquid carrier, in which said active compound is moderately soluble.

5. A kit for preparing a device for administering an active compound transdermally to a subject's skin, having a delayed onset of delivery, said kit comprising:
    a first layer comprising a polymeric matrix impregnated with said active compound, said compound and matrix being selected to obtain a first compound diffusion coefficient of about $10^{-5}$ to about $10^{-10}$ cm$^2$/sec in said matrix;
    a second layer not in contact with said first layer, comprising an adhesive capable of adhering to said first layer and to said subject's skin, said second layer having a second diffusion coefficient of about $10^{-5}$ to about $10^{-10}$ cm$^2$/sec in said matrix, wherein said second layer is substantially devoid of said active compound.

6. The kit of claim 5, which further comprises:
    a backing layer laminated to said first layer, wherein said backing layer is substantially impermeable to said compound.

7. The kit of claim 6 which further comprises:
    a backing layer laminated to said second layer.

8. The kit of claim 6 which further comprises:
    a release liner laminated to said second layer, opposite said backing layer.

9. The kit of claim 5 which further comprises:
    a backing layer laminated to said first and second layers, wherein said backing layer is substantially impermeable to said compound.

10. The kit of claim 9 which further comprises:
    a release liner laminated to said first and second layers, opposite said backing layer.

11. The kit of claim 5 wherein said active compound is selected from the group consisting of nitroglycerine and nicotine.

12. A device for administering an active compound transdermally following application to a subject's skin, having a delayed onset of delivery, said device consisting essentially of:
    a contact layer comprising a skin contact adhesive, substantially devoid of active compound at the time of application, which is permeable to said active compound in the absence of an activator;
    a backing layer comprising a thin, flexible material which is substantially impermeable to said active compound, which is laminated to said contact layer, and together with said contact layer defines a reservoir void between said contact layer and said backing layer; and
    within said reservoir void, a rupturable capsule containing said active compound.

13. The device of claim 12, which further consists essentially of:
    a wick layer of a porous fabric, laminated between said contact layer and said reservoir void.

14. The device of claim 13 wherein said wick layer is a non-woven fabric.

15. The device of claim 12 which further consists essentially of:

a structural support layer, laminated between said contact layer and said reservoir void, which is a polymer film or adhesive film which is permeable to said active compound.

16. The device of claim 13 which further consists essentially of:

a structural support layer, laminated between said contact layer and said wick layer, which is a polymer film or adhesive film which is permeable to said active compound.

17. The device of claim 12 which further consists essentially of:

a delay membrane laminated between said reservoir void and said contact layer, wherein said delay membrane is fabricated from a material selected from the group consisting of microporous polypropylene, microporous polyethylene, microporous polytetrafluoroethylene, dense polyurethane, dense polyacrylate, and dense polyisobutylene.

18. The device of claim 12 wherein active compound is administered through substantially the entire contact area between said device and said subject's skin.

19. The device of claim 12 wherein said rupturable capsule contains a volatile compound, and wherein said capsule is not permeable to said volatile compound.

20. The device of claim 19 wherein said volatile compound is selected from the group consisting of ethanol, ethyl acetate, acetone, methanol, tetrahydrofuran, and nicotine.

21. The device of claim 12 wherein said rupturable capsule has a rupturable heat seal.

22. The device of claim 12 wherein said rupturable capsule consists essentially of friable glass, friable silica, or a friable brittle polymer.

23. The device of claim 22, wherein said rupturable capsule is scored to facilitate rupture.

* * * * *